US006365617B1

(12) United States Patent
McComsey et al.

(10) Patent No.: US 6,365,617 B1
(45) Date of Patent: Apr. 2, 2002

(54) INDOLE AND INDAZOLE UREA-PEPTOIDS AS THROMBIN RECEPTOR ANTAGONISTS

(75) Inventors: David F. McComsey, Warminster, PA (US); William J. Hoekstra, Chapel Hill, NC (US); Bruce E. Maryanoff, Forest Grove; Han-Cheng Zhang, Lansdale, both of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/603,229

(22) Filed: Jun. 26, 2000

Related U.S. Application Data
(60) Provisional application No. 60/141,555, filed on Jun. 29, 1999.

(51) Int. Cl.$^7$ .......................... A61K 31/416; A61P 7/02; C07D 403/06
(52) U.S. Cl. ................. 514/403; 546/275.7; 546/277.1; 548/362.5; 548/468
(58) Field of Search .............................. 548/362.5, 468; 514/403

(56) References Cited

U.S. PATENT DOCUMENTS

| | | |
|---|---|---|
| 4,977,153 A | 12/1990 | Louis et al. |
| 5,439,906 A | 8/1995 | Bock et al. |
| 5,530,026 A | 6/1996 | Gaudreault et al. |
| 6,017,890 A | 1/2000 | Hoekstra et al. |

FOREIGN PATENT DOCUMENTS

| | | |
|---|---|---|
| CA | 2011222 A1 | 3/1990 |
| EP | 0385850 A1 | 7/1990 |
| WO | WO 92/14750 A1 | 3/1992 |
| WO | WO 93/18026 A1 | 9/1993 |
| WO | WO 99/00357 A1 | 1/1999 |
| WO | WO 99/33798 A1 | 7/1999 |
| WO | WO 99/42475 A1 | 8/1999 |
| WO | WO 99/42475 | 8/1999 |

OTHER PUBLICATIONS

Andrade–Gordon et al., Chemical Abstracts, vol. 132, No. 44502, (1999).*
"Approaches to the Synthesis of Ureapeptoid Peptidomimetics" John A. W. Kruijtzer et al., Tetrahedron Letters, vol. 38, No. 30, pp. 5335–8, 1997.
"Cloning and Characterization of Human Proteas–Activated Receptor 4", Wen–Feng Xu et al., Proc. Natl. Acad. Sci. USA. vol. 95. Jun. 1998, pp. 6642–6646.
"Molecular Cloning of a Potential Proteinase Activated Receptor ", Sverker Nystedt et al., Proc. Natl. Acad. Sci. USA. vol. 91, Sep. 1994, pp. 9208–9212.

"Thrombin–Induced Events in Non–Platelet Cells are Mediated by the Unique Proteolytic Mechanism Established for the Cloned Platelet Thrombin Receptor", David T. Hung, et al., The Journal of Cell Biology, vol. 116, No. 3, Feb. 1992, pp. 827–832.
"Thrombin Receptor Activation Causes Rapid Neural Cell Rounding and Nuerite Retraction Independent of Classic Second Messengers", Kees Jalink et al., The Journal of Cell Biology, vol. 118, No. 2, Jul. 1992, pp. 411–419.
"Thrombin–Induced Expression of Endothelial P–Selectin and Intercellular Adhesion Molecule–1: A Mechanism for Stabilizing Neutrophil Adhesion", Yasuo Suguma et al., The Journal of Cell Biology, vol. 119, No. 4, Nov. 1992, pp. 935–944.
"Molecular Cloning of a Functional Thrombin Receptor Reveals a Novel Proteolytic Mechanism of Receptor Activation", Thein–Khal H. Vu et al., Cell. vol. 64, Mar. 1991, pp. 1057–1068.
"Response of a Human Megarkaryocytic Cell Line to Thrombin: Increase in Intracellular Free Calcium and Mitogen Release", Cindy L. A. Jones, et al., Biochemica et Bioophysica Acta. 1136, 1992, pp. 272–282.
"Thrombin Effects on Osteoblastic Cells–II. Structure–Function Relationships" Dimitrius N. Tatakis et al., Biochemical and Biophysical Research Communications, vol. 174, No. 1, Jan. 1991, pp. 181–188.
"Condensed Heteroaromatic Ring Systems –XIII. One–Step Synthesis of 2–Substituted 1–Methylsulfoonylindoles from N–(2–Halophenyl) Methanesulfonamides", Takao Sakamoto et al., Chem. Pharm. Bull., No. 4, Sep. 1987, pp. 1305–1308.
"An Antibody Against the Exosite of the Cloned Thrombin Receptor Inhibits Experimental Arterial Thrombosis in the African Green Monkey", Jacquelynn J. Cook et al., Basic Science Reports, Oct. 1994, pp. 2961–2971.
"Protease–Activated Receptor 3 is a Second Thrombin Receptor in Humans", Hiriaki Ishihara, Nature, vol. 386, Apr. 1997, pp. 502–508.
"Heterocycle–Peptide Hybrid Compounds, Aminotriazole–Containing Agonists of the Thrombin Receptor (PAR–1)", David F. McComsey et al., Bioorganic & Medicinal Chemistry Letters 9 (1999), pp. 1423–1428.

(List continued on next page.)

Primary Examiner—Robert W. Ramsuer
(74) Attorney, Agent, or Firm—Hal B. Woodrow

(57) ABSTRACT

The invention is directed to novel indole and indazole urea-peptoid compounds which are useful as thrombin receptor antagonists for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders. Pharmaceutical compositions comprising the substituted indole and indazole urea-peptoid compounds of the present invention and methods of treating conditions mediated by the thrombin receptor are also disclosed.

19 Claims, No Drawings

OTHER PUBLICATIONS

"Design, Synthesis, and Biological Characterization of a Peptide–Mimetic Antagonist for a Tethered–Ligand Receptor" Patricia Andrade–Gordon et al., PNAS, vol. 96, No. 22, Oct. 26, 1999, pp. 12257–12262.

"Thrombin Receptor (PAR–1) Antagoonist, Heterocycle–Based Peptidomimetics of the SFLLR Agonist Motif", William J. Hoekstra et al., Bioorganic & Medicinal Chemisty Letters 8, (1998), pp. 1649–1654.

"Development of Potent Thrombin Receptor Antagonist Peptides", Michael S. Bernatowicz et al., J. Med. Chem., 1996, vol. 39, No. 25, pp. 4879–4887.

"Design, Synthesis, and Structure–Activity Relationship for a Series of Factor XA Inhibitors Containing the Benzimidazoone Nucleus as a Central Template", Charles K. Marlowe et al., Medicinal Chemistry, COR Therapeutics, Inc., Abstract.

"Novel Indole–Based Peptidomimetics as Potent Thrombin Receptor (PAR–1) Antagonists", Han Cheng Zhang et al., The R. W. Johnson Pharmaceutical Research Institute, Abstract.

\* cited by examiner

INDOLE AND INDAZOLE UREA-PEPTOIDS AS THROMBIN RECEPTOR ANTAGONISTS

This application claims the benefit of provisional application 60/141,555 filed Jun. 29, 1999.

FIELD OF THE INVENTION

This invention relates to certain novel thrombin receptor antagonists, their synthesis and their use for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders.

BACKGROUND OF THE INVENTION

Thrombin is an important serine protease in hemostasis and thrombosis. One of the key actions of thrombin is cellular modulation via receptor activation. A functional human thrombin receptor (PAR-1), cloned by Coughlin in 1991 (T.-K. Vu, *Cell* 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence, which has an SFLLRN (Ser-Phe-Leu-Leu-Arg-Asn) N-terminus acting as a tethered ligand to recognize a site on the receptor, can trigger activation and signal transduction leading to platelet aggregation. Since 1991, three other protease-activated receptors with extensive homology to the thrombin receptor, "PAR-2" (S. Nystedt, *Proc. Natl. Acad. Sci USA* 1994, 91, 9208), "PAR-3" (H. Ishihara, *Nature* 1997, 386, 502), and "PAR-4" (W.-F. Xu, *Proc. Natl. Acad. Sci USA* 1998, 95, 6642), have been cloned. Thrombin receptor (PAR-1) specific antibody-induced blockade of the platelet thrombin receptor has shown efficacy against arterial thrombosis in vivo (J. J. Cook *Circulation* 1995, 91, 2961). Hence, antagonists of the thrombin receptor (PAR-1) are useful to block these protease-activated receptors and, as such, may be used to treat platelet mediated thrombotic disorders such as myocardial infarction, stroke, restenosis, angina, atherosclerosis, and ischemic conditions.

The thrombin receptor (PAR-1) has also been identified on other cell types: endothelial, fibroblast, renal, osteosarcoma, smooth muscle, myocytes, tumor, and neuronal/glia. Thrombin activation of endothelial cells upregulates P-selectin to induce polymorphonuclear leukocyte adhesion—an inflammatory response of the vessel wall (Y. Sugama, *J. Cell Biol.* 1992, 119, 935). In fibroblasts, thrombin receptor (PAR-1) activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174, 181). Thrombin has been implicated in the regulation and retraction of neurons (K. Jalink, *J. Cell. Biol.* 1992, 118, 411). Therefore, in this context, the antagonist compounds of this invention may also be useful against inflammation, osteoporosis, Angiogenesis related disorders, cancer, neurodegenerative disorders, hypertension, heart failure, arrhythmia, glomerulonephritis.

The compounds of the present invention are a structurally novel class of indole and indazole urea-peptoids represented by the general formula (I) below.

SUMMARY OF THE INVENTION

The present invention is directed to structurally novel compounds resented by the following general formula (I):

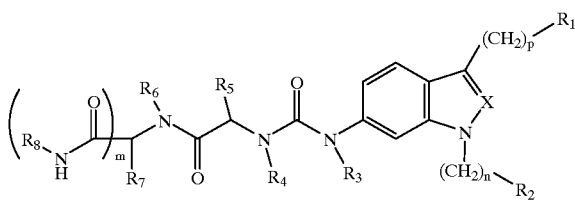

wherein:

$R_1$ is selected from amino, $C_1$–$C_8$ alkylamino, $C_1$–$C_8$ dialkylamino, arylamino, ar$C_1$–$C_8$ alkylamino, $C_3$–$C_8$ cycloalkylamino, heteroalkyl$C_1$–$C_8$ alkylamino, heteroalkyl$C_1$–$C_8$ alkyl-N-methylamino, $C_1$–$C_8$ dialkylamino $C_1$–$C_8$ alkylamino, —N($C_1$–$C_8$alkyl)—$C_1$–$C_8$alkyl-N($C_1$–$C_8$alkyl)$_2$, —N($C_1$–$C_8$ alkyl)($C_1$–$C_8$ alkenyl), —N($C_1$–$C_8$alkyl)($C_3$–$C_8$cycloalkyl), heteroalkyl or substituted heteroalkyl, wherein the substituent on the heteroalkyl is selected from oxo, amino, $C_1$–$C_8$ alkoxy, $C_1$–$C_8$ alkyl, $C_1$–$C_8$ alkylamino or $C_1$–$C_8$ dialkylamino;

$R_2$ is selected from unsubstituted or substituted aryl, ar$C_1$–$C_8$ alkyl, $C_3$–$C_8$cycoalkyl or heteroaryl, wherein the substituents on the aryl, aralkyl, cycloalkyl or heteroaryl group are independently selected from one or more of halogen, nitro, amino, cyano, hydroxyalkyl, $C_1$–$C_8$ alkyl, $C_1$–$C_8$ alkoxy, $C_1$–$C_8$alkoxycarbonyl, acetyl, fluorinated $C_1$–$C_4$ alkyl, fluorinated $C_1$–$C_4$ alkoxy or $C_1$–$C_4$ alkylsulfonyl;

$R_3$ is selected from H or $C_1$–$C_8$ alkyl;

$R_4$ and $R_5$ are each selected from H, $C_1$–$C_8$ alkyl, amino $C_1$–$C_8$ alkyl, amidino $C_1$–$C_8$ alkyl, guanidino $C_1$–$C_8$ alkyl, aryl, aryl $C_1$–$C_8$ alkyl, substituted aryl, substituted aryl$C_1$–$C_8$ alkyl, heteroaryl, heteroaryl $C_1$–$C_8$ alkyl, substituted heteroaryl, substituted heteroaryl $C_1$–$C_8$ alkyl, cyclo $C_3$–$C_6$ alkyl or substituted cyclo$C_3$–$C_6$alkyl, wherein the substituents on the aryl, aralkyl, cycloalkyl or heteroaryl group are independently selected from one or more of halogen, nitro, amino, amidino, guanidino, cyano, hydroxyalkyl, $C_1$–$C_8$ alkyl, $C_1$–$C_8$ alkoxy, $C_1$–$C_8$ alkoxycarbonyl, acetyl, fluorinated $C_1$–$C_4$ alkyl, fluorinated $C_1$–$C_4$ alkoxy or $C_1$–$C_4$ alkylsulfonyl;

$R_6$ and $R_7$ are each selected from H, $C_1$–$C_8$ alkyl, amino-$C_1$–$C_8$ alkyl, amino-$C_3$–$C_8$ cycloalkyl, amidino $C_1$–$C_8$ alkyl, guanidino $C_1$–$C_8$ alkyl, aryl, substituted aryl, aryl $C_1$–$C_8$ alkyl, substituted aryl $C_1$–$C_8$ alkyl, heteroaryl $C_1$–$C_8$ alkyl or substituted heteroaryl $C_1$–$C_8$ alkyl, wherein the substituents on the aryl, aralkyl, cycloalkyl or heteroaryl group are independently selected from one or more of halogen, nitro, amino, amidino, guanidino, cyano, hydroxyalkyl, $C_1$–$C_8$ alkyl, $C_1$–$C_8$ alkoxy, $C_1$–$C_8$ alkoxycarbonyl, acetyl, fluorinated $C_1$–$C_4$ alkyl, luorinated $C_1$–$C_4$ alkoxy or $C_1$–$C_4$ alkylsulfonyl;

Either $R_5$ or $R_7$ must be H when m is 1; in addition, when $R_5$ is H, then $R_4$ cannot be H; and, when $R_7$ is H, then $R_6$ cannot be H;

$R_8$ is selected from H, $C_1$–$C_8$ alkyl, amino $C_1$–$C_0$ alkyl, allyl, $C_3$–$C_8$ cycloalkyl, substituted $C_3$–$C_8$ cycloalkyl, aryl, substituted aryl, ar $C_1$–$C_8$ alkyl, substituted ar $C_1$–$C_8$ alkyl, heteroaryl, substituted heteroaryl, heteroaryl $C_1$–$C_8$ alkyl or substituted heteroaryl $C_1$–$C_8$ alkyl, wherein the substituents on the aryl, aralkyl, cycloalkyl or heteroaryl group are independently selected from one or more of halogen, nitro, amino, amidino, guanidino, cyano, hydroxyalkyl, $C_1$–$C_8$ alkyl, $C_1$–$C_8$ alkoxy, $C_1$–$C_8$ alkoxycarbonyl, acetyl, fluorinated $C_1$–$C_4$ alkyl, fluorinated $C_1$–$C_4$ alkoxy or $C_1$–$C_4$ alkylsulfonyl;

X is CH or N;

n is an integer selected from 0, 1, 2 or 3;

m is an integer selected from 0 or 1;

p is an integer selected from 1 or 2; and, pharmaceutically acceptable salts thereof.

In one embodiment of the invention is the compound of formula (I) wherein $R_1$ is selected from dimethylamino, diethylamino, di-(n-propyl)amino,

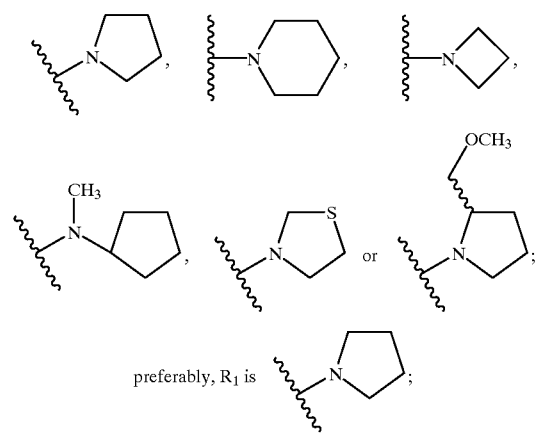

$R_2$ is selected from unsubstituted or substituted aryl, $arC_1$–$C_6$ alkyl, $C_3$–$C_6$ cycloalkyl or heteroaryl, where the substituents on the aryl, aralkyl, cycloalkyl or heteroaryl group are independently selected from one to three substituents selected from halogen, cyano, $C_1$–$C_4$ alkyl, $C_1$–$C_4$ alkoxy, $C_1$–$C_4$ alkoxycarbonyl, fluorinated $C_1$–$C_4$ alkyl, fluorinated $C_1$–$C_4$ alkoxy or $C_1$–$C_4$ alkylsulfonyl; preferably, $R_2$ is unsubstituted or substituted phenyl wherein the substituent is one or two substituents selected from fluorine, chlorine, iodine, methyl, cyano or trifluoromethyl;

$R_3$ is selected from H or $C_1$–$C_4$ alkyl; preferably, $R_3$ is H;

$R_4$ and $R_5$ are each independently selected from H, $C_1$–$C_4$ alkyl, $aminoC_1$–$C_6$ alkyl, $amidinoC_1$–$C_6$ alkyl, $guanidinoC_1$–$C_6$ alkyl, aryl, $arC_1$–$C_8$ alkyl, substituted aryl, or substituted $arC_1$–$C_8$ alkyl, wherein the substituents on the aryl or aralkyl are independently selected from one or two of halogen, nitro, amino, amidino, guanidino, cyano, hydroxyalkyl, $C_1$–$C_6$alkyl, $C_1$–$C_6$alkoxy, $C_1$–$C_6$ alkoxycarbonyl, acetyl, fluorinated $C_1$–$C_4$ alkyl, fluorinated $C_1$–$C_4$ alkoxy or $C_1$–$C_4$ alkylsulfonyl;

$R_6$ and $R_7$ are each independently selected from H, $C_1$–$C_4$ alkyl, $aminoC_1$–$C_6$ alkyl, $amidinoC_1$–$C_6$ alkyl, $guanidinoC_1$–$C_6$ alkyl, aryl, substituted aryl, $arC_1$–$C_6$ alkyl, substituted $arC_1$–$C_6$ alkyl, $C_3$–$C_6$ $cycloalkylC_1$–$C_6$ alkyl, $heteroarylC_1$–$C_6$ alkyl or substituted $heteroarylC_1$–$C_6$ alkyl, wherein the substituents on the aryl, aralkyl, or heteroaryl group are independently selected from one or two of halogen, nitro, amino, amidino, guanidino, cyano, hydroxyalkyl, $C_1$–$C_6$ alkyl, $C_1$–$C_6$ alkoxy, $C_1$–$C_6$ alkoxycarbonyl, acetyl, fluorinated $C_1$–$C_4$ alkyl, fluorinated $C_1$–$C_4$ alkoxy or $C_1$–$C_4$ alkylsulfonyl;

preferably, $R_4$, $R_5$, $R_6$, and $R_7$ are each independently selected from H, $aminoC_1$–$C_5$ alkyl, $amidinoC_1$–$C_5$ alkyl, $guanidinoC_1$–$C_5$ alkyl, $C_3$–$C_6$ $cycloalkylC_1$–$C_6$ alkyl, $heteroarylC_1$–$C_6$ alkyl, benzyl or substituted benzyl wherein the substituents on the benzyl are independently selected from one or two of chlorine, fluorine, methyl or trifluoromethyl;

$R_8$ is selected from H, $C_1$–$C_6$alkyl, $aminoC_1$–$C_6$ alkyl, aryl, substituted aryl, $arC_1$–$C_6$ alkyl, or substituted $arC_1$–$C_6$ alkyl, wherein the substituents on the aryl or aralkyl group are independently selected from one or more of halogen, nitro, amino, amidino, guanidino, cyano, hydroxyalkyl, $C_1$–$C_6$alkyl, $C_1$–$C_6$ alkoxy, $C_1$–$C_6$ alkoxycarbonyl, acetyl, fluorinated $C_1$–$C_4$ alkyl, fluorinated $C_1$–$C_4$ alkoxy or $C_1$–$C_4$ alkylsulfonyl; preferably, $R_8$ is benzyl;

n and p are both 1;

provided that when m is one, then one of $R_5$ or $R_7$ must be hydrogen;

and provided further that when $R_5$ is hydrogen, then $R_4$ cannot be hydrogen; and, when $R_7$ is hydrogen, then $R_6$ cannot be hydrogen;

and pharmaceutically acceptable salts thereof.

In a class of the invention is the compound wherein $R_2$ is 2,6-dichlorophenyl;

and all other variables are as defined above;

provided that when m is one, then one of $R_5$ or $R_7$ must be hydrogen;

and provided further that when $R_5$ is hydrogen, then $R_4$ cannot be hydrogen; and, when $R_7$ is hydrogen, then $R_6$ cannot be hydrogen;

and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, athersclerosis, ischemic conditions, hypertension, heart failure, arrhythmia, glomerulonephritis, osteoporosis, Angiogenesis related disorders, cancer, neurodegenerative disorders or a variety of vaso-occlusive disorders in a subject in need thereof comprising administering to the subject a therapeutically effective amount of any of the compounds or pharmaceutical compositions described above. In a preferred embodiment, the therapeutically effective amount of the compound is from about 0.1 mg/kg/day to about 300 mg/kg/day.

Also included in the invention is the use of any of the compounds described above for the preparation of a medicament for a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, athersclerosis, ischemic conditions, hypertension, heart failure, arrhythmia, glomerulonephritis, osteoporosis, Angiogenesis related disorders, cancer, neurodegenerative disorders or a variety of vaso-occlusive disorders in a subject in need thereof.

DETAILED DESCRIPTION OF THE INVENTION

More particularly, the present invention is directed to compounds of the following formula (I):

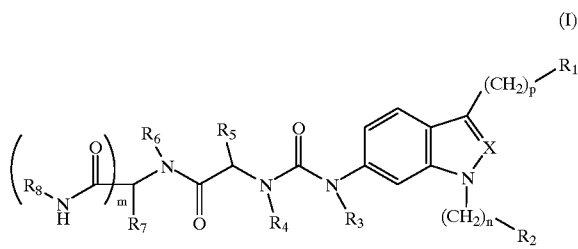

wherein $R_1$, $R_2$, $R_3$, $R_4$, $R_5$, $R_6$, $R_7$, $R_8$, X, m, n, and p are as previously defined.

The compounds of the present invention are thrombin receptor antagonists and as such are useful in treating thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder, neurodegenerative disorders, Angiogenesis related disorders and cancer. These compounds are also useful as antithrombotics in conjunction with fibrinolytic therapy (e.g., t-PA or streptokinase).

When a particular group is "substituted" (e.g., Phe, aryl, heteroalkyl, heteroaryl), that group may have one or more substituents, preferably from one to five substituents, more preferably from one to three substituents, most preferably from one to two substituents, independently selected from the list of substituents.

Under standard nomenclature used throughout this disclosure, the terminal portion of the designated side chain is described first, followed by the adjacent functionality toward the point of attachment. Thus, for example, a "phenyl$C_1$–$C_6$ alkylamido$C_1$–$C_6$alkyl" substituent refers to a group of the formula

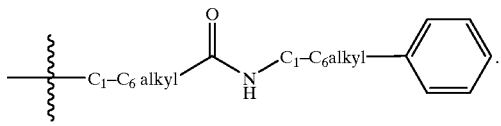

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms or any number within this range.

The term "aryl" as used herein refers to an unsubstituted or substituted aromatic group such as phenyl and naphthyl.

The term "heteroalkyl" as used herein represents an unsubstituted or substituted stable three to seven membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heteroalkyl group may be attached at any heteroatom or carbon atom which results in the creation of a stable structure. Examples of such heteroalkyl groups include, but are not limited to azetidinyl, piperidinyl, pyrrolidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

Preferred heteroalkyl groups include pyrrolidinyl, piperidinyl, piperazinyl, morpholinyl, azetidinyl and tetrahydrothiazolyl.

The term "heteroaryl" as used herein represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom that results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl. Prefered heteroaryl groups include pyridyl, pyrrolyl, pyrazinyl, thiadiazolyl, pyrazolyl, thienyl, triazolyl and quinolinyl.

The term "aralkyl" means an alkyl group substituted with one, two or three aryl groups (e.g., benzyl, phenylethyl, diphenylmethyl, triphenylmethyl). Similarly, the term "aralkoxy" indicates an alkoxy group substituted with an aryl group (e.g., benzyloxy). The term aminoalkyl refers to an alkyl group substituted with an amino group (i.e., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-[alkyl]$_2$).

The term "acyl" as used herein mneans an organic radical having 1 to 6 carbon atoms (branched or straight chain) derived from an organic acid by removal of the hydroxyl group.

The term "oxo" refers to the group =O.

The term "carbonyl" refers to the group C(O).

The term "halogen" shall include iodine, bromine, chlorine and fluorine.

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

Particularly preferred representative compounds of the present invention and their biological data are shown in Table 1 and Table 2, following. Table 1 and Table 2 each contain $IC_{50}$ values ($\mu M$) against platelet aggregation stimulated by thrombin and $IC_{50}$ values ($\mu M$) of the compounds in a thrombin receptor binding assay. The assays used to determine the biological data for the instant compounds are further described herein.

TABLE 1

Thrombin Receptor Antagonists

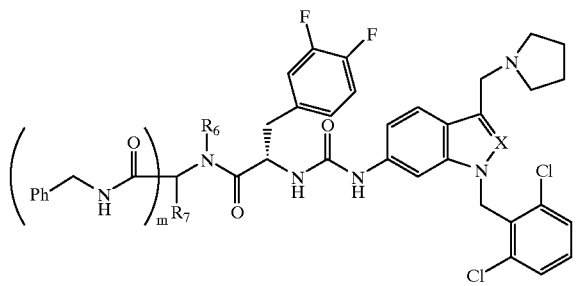

| Cmpd | R$_6$ | X | R$_7$ | m | GFP Aggr.* IC$_{50}$, $\mu M$ | Recptr Bdg.** IC$_{50}$, $\mu M$ |
|---|---|---|---|---|---|---|
| 1 | (CH$_2$)$_2$NH$_2$ | N | H | 1 | 1.3 | 0.5 |
| 2 | (CH$_2$)$_2$NH$_2$ | CH | H | 1 | 1.7 | 0.3 |
| 3 | (CH$_2$)$_4$NH$_2$ | N | H | 1 | 0.26 | 0.3 |
| 4 | (CH$_2$)$_4$NH$_2$ | CH | H | i | 0.26 | 0.22 |
| 5 | PhCH$_2$ | CH | H | 1 | 22 | 0.38 |
| 6 | 2-ThienylCH$_2$ | CH | (CH$_2$)$_2$NH$_2$ | 0 | 0.6 | 10.3 |
| 7 | c-C$_6$H$_{11}$CH$_2$ | CH | (CH$_2$)$_2$NH$_2$ | 0 | 1.0 | 8.8 |
| 8 | 4-PyridylCH$_2$ | CH | (CH$_2$)$_2$NH$_2$ | 0 | 0.40 | 29 |
| 9 | H | N | (CH$_2$)$_2$NH$_2$ | 0 | 0.26 | 0.10 |
| 10 | 4-PyridylCH$_2$ | CH | (CH$_2$)$_3$NH$_2$ | 0 | 0.51 | 0.10 |
| 11 | H | CH | (CH$_2$)$_3$NH$_2$ | 0 | 1.7 | 0.10 |
| 12 | H | CH | CH$_2$NH$_2$ | 0 | 0.99 | 0.07 |

*GFP Aggr. Thrombin-Induced Gel-Filtered Platelet Aggregation Assay
**Recptr Bdg Thrombin Receptor Binding Assay

TABLE 2

Thrombin Receptor Antagonists

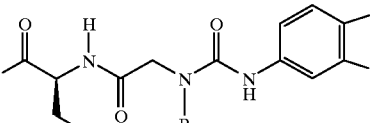

| Cmpd | $R_4$ | GFP Aggr.* $IC_{50}, \mu M$ | Recptr Bdg.** $IC_{50}, \mu M$ |
|---|---|---|---|
| 13 | $(CH_2)_5NH_2$ | 1.0 | >100 |
| 14 | $4\text{-ClPhCH}_2$ | 6.3 | 6.9 |
| 15 | $4\text{-FPhCH}_2$ | 2.1 | 8.1 |

The antagonists of the present invention may be prepared via either solution-phase or solid-phase methods. In general, the compounds may be synthesized in solution following Generic Scheme A or Generic Scheme B.

As shown in Generic Scheme A, the 6-nitroindole A1 may be alkylated with the appropriate halide and a base such as potassium or cesium carbonate in a dipolar aprotic solvent such as DMF or THF. Upon work-up, the crude intermediate may be reduced with a reducing agent such as iron and acetic acid or dimethyl hydrazine to give the amine A2. The Fmoc protected amino-acid A3, which may be commercially available or prepared by alkylation of $R_6NH_2$ with a 2-bromo acetic acid followed by Fmoc protection, is coupled to an $R_8$ substituted amine using classical coupling agents such as DCC or DIC with HOBT in a dipolar aprotic solvent such as ACN or DMF. The Fmoc group is removed with a secondary amine such as diethylamine in a dipolar aprotic solvent such as ACN or DMF. The resultant amine may then be coupled with bromoacetic acid in DCC and the intermediate bromide alkylated with a $R_4$ substituted amine in the presence of triethylamine to afford the amine A4. Alternatively, the amine may be coupled with another Fmoc protected amino-acid followed by Fmoc deprotection to afford the amine A4. The amine A2 is reacted with a phosgene equivalent such as 4-nitrophenyl chloroformate, phosgene or "$COCl_2$", phenyl chloroformate, triphosgene or "$(CCl_3O)_2CO$", carbonyldiimidazole, diethyl carbonate or diphenyl carbonate and DIEA, then combined with A4 to give the urea A5. The urea A5 is then added to a preformed Mannich intermediate from reaction of an amine with formaldehyde in acetic acid to afford (after TFA deprotection of side-chains if necessary) the target A6.

GENERIC SCHEME A

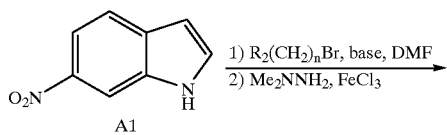

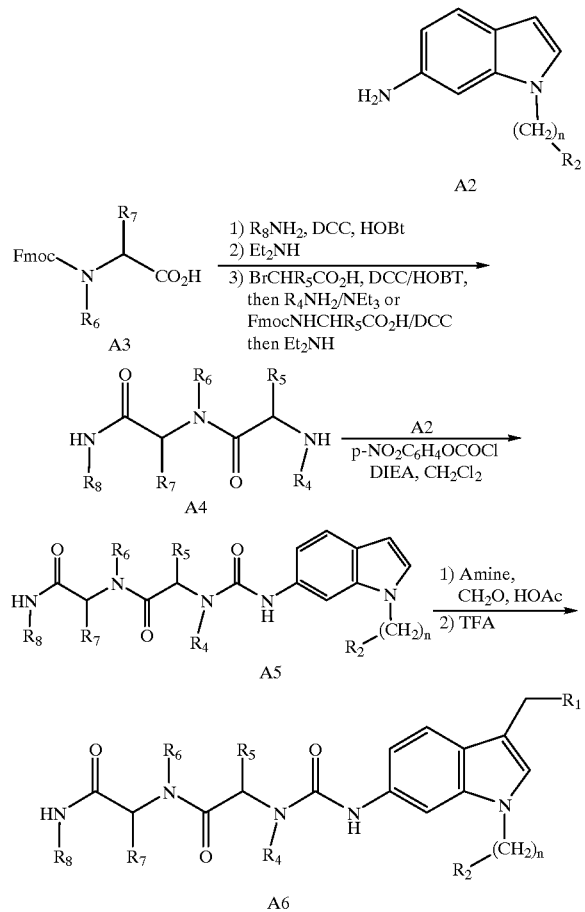

As shown in Generic Scheme B, the indole A1 is converted to indazole B1 with sodium nitrite and HCl and then reductively aminated with an amine and a reducing agent such as sodium triacetoxyborohydride to give B2. B2 was then alkylated with an appropriate alkyl halide and a base such as potassium hydroxide in a dipolar aprotic solvent such as DMF, followed by reduction of the nitro group using classical reducing agents such as tin chloride and HCl to give the amine B3. The amine B3 was reacted with a phosgene equivalent and DIEA then combined with amine A4, as prepared above, to give the desired urea; again, deprotection of side-chain protecting groups with an acid such as TFA may be required to afford the indazole targets B4.

GENERIC SCHEME B

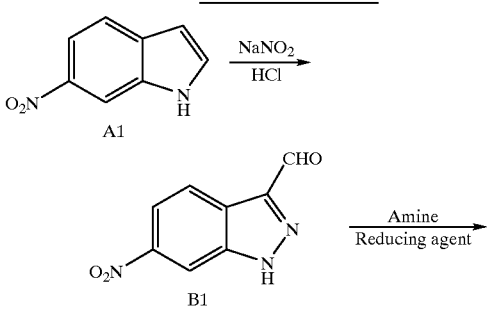

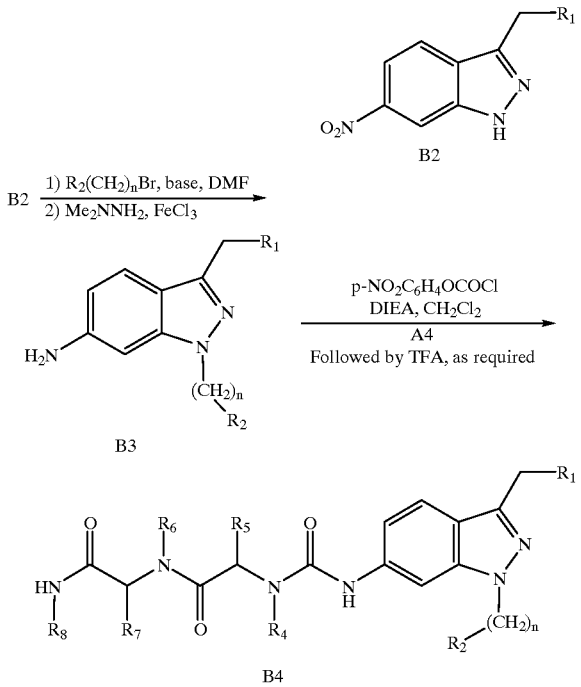

The side-chain amine in antagonists such as Compound 1 and Compound 6 may be converted to other functional groups such as acetamidine and guanidine by using standard procedures. For example, the acetamidine and guanidine groups can be introduced by treating the side-chain amine with S-2-naphthylmethyl thioacetimidate hydrobromide and 2-methyl-2-thiopseudourea, respectively.

Extending the carbon chain from p being 1 to n being 2 at the 3-position of the indole [see general formula (I), X=CH] may be achieved by treating the dimethylamino Mannich base (when p is 1, $R_1$ is $NMe_2$) with KCN followed by reducing the cyano group to an amine.

Extending the carbon chain from p being 1 to n being 2 at the 3-position of the indazole [see general formula (I), X=N] may be introduced in the intermediate B1 (Generic Scheme B) via aldehyde-nitromethane condensation followed by reduction of the resulting α,β-unsaturated nitro compounds to saturated amine.

The utility of the compounds to treat PAR-1 mediated disorders (e.g., thrombotic disorders) can be determined according to the procedures described herein. The present invention therefore provides a method of treating PAR-1 mediated disorders (e.g., thrombotic disorders) in a subject in need thereof which comprises administering any of the compounds as defined herein in a quantity effective to treat PAR-1 mediated disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.03 mg/kg to about 100 mg/kg (preferred from about 0.1 mg/kg to about 30 mg/kg) of a compound of the present invention and may be given at a dosage from about 0.1 mg/kg/day to about 300 mg/kg/day (preferred from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating PAR-1 mediated disorders (e.g., thrombotic disorders) described in the present invention may also be carried out using a pharmaceutical composition comprising any of the compounds as defined herein and a pharmaceutically acceptable carrier. The pharmaceutical composition may contain between about 0.01 mg to about 100 mg, preferably from about 5 mg to about 50 mg of the compound and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of PAR-1 mediated disorders (e.g., thrombotic disorders) is required.

The daily dosage of the products may be varied over a wide range from about 0.01 mg to about 1,000 mg per adult human per day. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 mg of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 mg/kg to about 10 mg/kg of body weight per day. The compounds may be administered on a regimen of about 1 time to about 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Biology

The compounds of the present invention are thrombin receptor (PAR-1) antagonists. The compounds interrupt platelet activation induced by thrombin's proteolytic cleavage of its platelet surface receptor, and thereby inhibit platelet aggregation. Such compounds are, therefore, useful in treating platelet-mediated thrombotic disorders (e.g., arterial and venous thrombosis, acute myocardial infarction, reocclusion following thrombolytic therapy and angioplasty, and a variety of vaso-occlusive disorders) and other PAR-1 mediated disorders.

In Vitro Thrombin Receptor Binding Assay

CHRF membranes (Jones, Biochim. Biophys. Acta 1992, 1136, 272) are thawed from −70° C., centrifuged at maximum speed for 5 min, washed twice with binding buffer (50 mM HEPES containing 5 mM $MgCl_2$ and 0.1% BSA), and re-suspended in binding buffer (25 μg/100 mL). 100 μL of membranes are added to the 24-Wallac plates and delivered to the Tomtech apparatus. In a typical experiment, 6 μL of samples (from a 125 μg/mL intermediary plate, 20% DMSO) and 44 μL buffer are delivered to the plates (final conc. of compounds is 3.7 μg/mL, 0.6% DMSO). Similarly, 6 μL 20% DMSO and 44 μL buffer are delivered to both column 1 (NSB) and column 12 (TB). 10 μL Ser-pFPhe-Har-Leu-Har-Lys-Tyr-$NH_2$ (721-40; 500 μM in deionized water) is added to column 1. 50 μL tritiated 721-40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are presoaked 3 h in 0.5% polyethylenimine in HEPES/0.1M N-acetylglucosamine) are set in saran wrap and dried for 3 min in the microwave, and placed in sample bags (Wallac 1450-432). 4.5 mL scintillation fluid (Wallac, Betaplate Scint 1205-440) is added. The bags are sealed, placed in filter cassettes (Wallac 1450-104), and analyzed on the microbeta counter.

In Vitro Inhibition Of Thrombin-induced Gel-filtered Platelet Aggregation Assay

The percentage of platelet aggregation is calculated as an increase in light transmission of compound-treated platelet concentrate vs. control-treated platelet concentrate. Human blood is obtained from drug free, normal donors in tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to $2×10^7$ platelets per sample. The following constituents are added to a siliconized cuvette: concentrated platelet filtrate and Tyrode's buffer (0.14M NaCl, 0.0027M KCl, 0.012M $NaHCO_3$, 0.76 mM $Na_2HPO4$, 0.0055M glucose, 2 mg/mL BSA and 5.0 mM HEPES @ pH 7.4) in an amount equal to 350 μL, 50 μL of 20 mM calcium and 50 μL of the test compound. Aggregation is monitored in a BIODATA aggregometer for the 3 min following the addition of agonist (thrombin 50 μL of 1 unit/mL).

The biological activity for representative compounds of the present invention are as previously shown in Table 1 and Table 2.

EXAMPLES

General Procedures:

Resins and protected amino acids were purchased from Novabiochem, Bachem Bioscience, Advanced ChemTech or Synthe Tech. All other chemicals were obtained from commercial suppliers and used without further purification. $^1H$ and $^{13}C$ NMR spectra were recorded on a Bruker AC 300B (300 MHz proton)or a Bruker AM-400 (400 MHz proton) spectrometer with $Me_4Si$ as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel GF plates. Flash column chromatography was conducted with flash column silica gel (40–63 μm) and column chromatography was conducted with standard silica gel. HPLC separations were carried out on three Waters PrepPak® Cartridges (25×100 mm, Bondapak® C18, 15–20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

In the examples and throughout this application, the following abbreviations have the meanings recited hereinafter:

| | |
|---|---|
| Ac | Acetyl |
| ACN | Acetonitrile |
| Bn | Benzyl |
| Boc | t-Butoxycarbonyl |
| DCC | 1,3-Dicyclohexylcarbodiimide |
| DCM | Dichloromethane |
| DEA | Diethylamine |
| DIC | Diisopropylcarbodiimide |
| DIEA | Diisopropylethylamine |
| DMAP | 4-Dimethylaminopyridine |
| DMF | N, N-Dimethylformamide |
| Et | Ethyl |
| Fmoc | 9-Fluorenylmethoxycarbonyl |
| h | Hour |
| HBTU | 2-(1H-Benzotriazole-1-yl)-1,1,3,3-tetramethyluronium hexafluorophosphate |
| HOAc | Acetic acid |
| HOBT | Hydroxybenzotriazole |
| i-Pr or iPr | Isopropyl |
| Me | Methyl |
| min | Minute |
| Pmc | 2,2,5,7,8-Pentamethylchroman-6-sulfonyl |
| Py | Pyridine |
| rt | room temperature |
| THF | Tetrahydrofuran |
| TFA | Trifluoroacetic acid |
| Tr | Triphenylmethyl |

Example 1

Synthesis of Compound 15 (See Scheme AA)

N-4-Fluorophenylmethyl-N-{[1-(2,6-dichlorophenyl)methyl-3-(1-pyrrolidinylmethyl)-1H-indol-6-yl]aminocarbonyl}-clycinyl-L-arginin-N-benzyl-amide (Compound 15)

As shown in Scheme AA, following, 6-Nitroindole AA1 (8.0 g, 49.2 mm) was dissolved in dry DMF (60 mL) under argon, cesium carbonate (16.0 g, 49.2 mm) was added and the mixture was stirred at about 45° C. for about 30 min. After cooling to about rt, the mixture was stirred while 2,6 dichlorobenzyl bromide (13.0 g, 54 mm) in DMF (40 mL)

was added over about 1 h; the reaction was then stirred at about rt for about 16 h. The solution was then added portionwise to water (1.6 L) with vigorous stirring, which precipitated a solid, and stirring was continued for about 3 h. The resulting yellow solid was filtered and washed with hexane (3×) and air-dried. The solid was combined in MeOH (150 mL) with charcoal (1.1 g, 92 mm), ferric chloride hexahydrate (0.54 g, 2.0 mm) and 1,1 dimethylhydrazine (27.2 g, 440 mm) and the mixture was refluxed for about 16 h. After cooling to about rt, the reaction was filtered through dicalite and the filtrate was evaporated in vacuo to a yellow solid. The solid was partitioned between 1N HCl (750 mL) and diethyl ether (750 mL). The solid was then combined with the aqueous acid solution, the pH was made greater than about pH 13 with 3N NaOH and extracted with DCM (2×, 400 mL). The DCM solution was washed with saturated NaHCO$_3$ (2×), brine, dried (K$_2$CO$_3$) and evaporated in vacuo to a solid, which was triturated with hexane (3×) to afford a light tan solid AA2.

Fmoc-arginine(PMC)-OH AA3 (3.83 g, 5.0 mm) and HOBT (0.76 g, 5.0 mm) were combined in acetonitrile (100 mL), benzylamine (0.54 g, 5.0 mm) was added in dropwise at about rt, followed by DCC (2.06 g, 10.0 mm) and stirred for about 16 h. The solid was filtered and the filtrate was evaporated in vacuo to an oil, which was dissolved in ethyl acetate (100 mL) and washed with saturated NaHCO$_3$ (2×), brine (2×), dried (Na$_2$SO$_4$) and was evaporated in vacuo to a solid, which was triturated with hexane (2×) to give a solid (impure with dicyclohexylurea). A portion of the solid (0.52 g, 0.70 mm) was dissolved in ACN (30 mL), diethyl amine (1.5 mL) was added and the reaction was stirred at about rt for about 1 h. The solution was evaporated in vacuo to a solid, which was triturated with hexane (3×) and evaporated in vacuo to a solid. The resulting solid was combined in ACN (20 mL) with bromoacetic acid (0.10 g, 0.70 mm) and HOBT (0.11 g, 0.7 mm). DCC (0.29 g, 1.4 mm) was added to the solution and the reaction was stirred at about rt for about 2 h. The solid was filtered and discarded and the filtrate was evaporated in vacuo to an oil. The oil was dissolved in ethyl acetate (25 mL) and washed with saturated NaHCO$_3$ (3×), brine (2×), dried (Na$_2$SO$_4$) and evaporated in vacuo to an oil. The resulting oil was dissolved in DCM (10 mL), 4-fluorobenzylamine (88 mg, 0.70 mm) and triethylamine (101 mg, 1.0 mm) were added and the reaction stirred at about rt for about 24 h. The solution was evaporated in vacuo to an oil, which was purified by column chromatography to afford amine AA4.

Amino-indole AA2 (142 mg, 0.49 mm) and DIEA (63 mg, 0.49 mm) in DCM (3 mL) were added to 4-nitrophenylchloroformate (99 mg, 0.49 mm) in dry DCM (120 mL) at about −20° C. and stirred at about -20° C. for about 30 min; the amine AA4 (380 mg, 0.49 mm) and DIEA (63 mg, 0.49 mm) in DCM (3 mL) were then added, stirred at about −20° C. for about 30 min and then at about rt for about 16 h. Solid urea AA5 precipitated out, was filtered and air dried. Pyrrolidine (90 mg, 1.25 mm) was added to glacial acetic acid (5.0 mL) under argon and formaldehyde (37%, 0.10 g, 1.25 mm) was added; the reaction was stirred at about rt for about 25 min. The indole urea AA5 (0.43 g, 0.42 mm) was added and the reaction stirred at about rt for about 2 h. The solution was evaporated in vacuo to an oil, which was partitioned between chloroform in 2-propanol (10:1, 75 mL) and 1N NaOH (30 mL). The organic layer was washed with saturated NaHCO$_3$ (2×), brine (2×) and dried (K$_2$CO$_3$), then evaporated in vacuo to a tan solid. This solid was stirred with TFA:DCM:anisole (50:50:1; 40 mL) at about rt for about 3 h and evaporated in vacuo to an oil. The resulting oil was triturated with ethyl ether (3×) to give the product Compound 15 as an off-white solid. H-1 NMR δ 1.4–2.0 (m, 8 aliphatics), 3.0–3.3 (m, 6H), 4.1 (dd, 2H), 4.2–4.4 (m, 5H), 4.6 (dd, 2H), 5.4 (s, 2H, CH$_2$), 7.05 (s, 1H, indole H$_2$), 7.1–7.7 (m, 14H, aromatics), 7.9 (s, 1H, indole H$_7$); MS m/z 828 (MH$^+$).

SCHEME AA

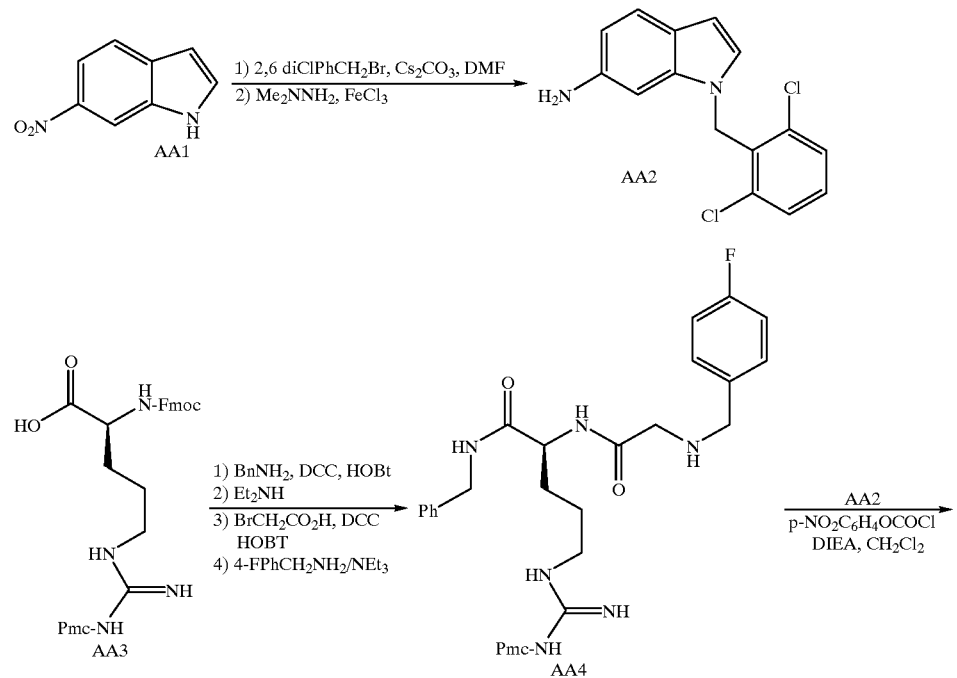

-continued

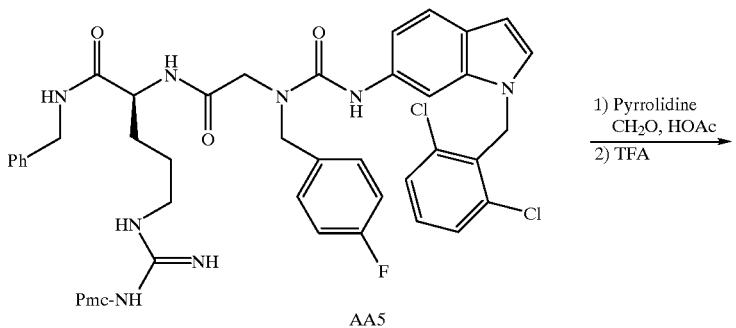

AA5

1) Pyrrolidine CH₂O, HOAc
2) TFA

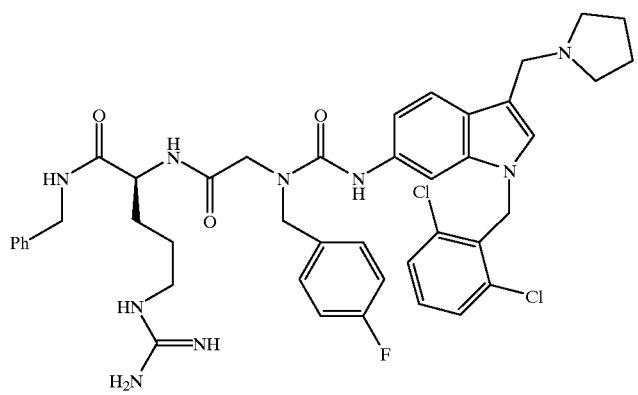

15

Example 2

Synthesis of Compound 6 (See Scheme AB)

Benzene Propanamide, N-(3-aminopropyl)-N-(2-thiophenemethyl)-α-[[[[[1-(2,6-dichlorophenyl)methyl]-3-(1-pyrrolidinylmethyl)-1H-indol-6-yl]amino]carbonyl]amino]-3,4-difluoro-, (αS)- (Compound 6)

As shown in Scheme AB, following, 2-Chlorotrityl chloride resin (4.5 g, 8.1 mmol) was stirred in dried DMF (80 mL) as 1,3-diaminopropane (AB1) (18.0 g, 243 mmol) was added. The reaction was stirred at about rt for about 20 h. The resin AB2 was filtered on a sintered glass funnel and washed with DMF (4×), MeOH (3×), and DCM (3×) and dried in vacuo to give the resin AB2. A portion of the resin AB2 (300 mg) was placed in a solid-phase hour-glass reactor and agitated (nitrogen bubbling) in DMF (8 mL) with 2-thiophenecarboxaldehyde (467 mg, 4.2 mmol) and HOAc (100 mL) for about 1.5 h. The solution was drawn off and the resin was washed with dried DMF (3×), suspended in dried DMF (8 mL) and then re-treated with 2-thiophenecarboxaldehyde (467 mg, 4.2 mmol) and HOAc (100 mL) for about another 0.5 h. The resulting solution was drawn off and the resin was washed with dried DMF (3×). To the resin was added dried DMF (8 mL) and MeOH (3 mL), then immediately followed by NaBH₄ (200 mg, 5.3 mmol). The mixture was agitated (nitrogen bubbling) at about rt for about 1.5 h and then filtered, washed with MeOH, DMF and DCM and dried in vacuo to afford the resin AB3. A portion of the resin AB3 (160 mg) was suspended in DMF (4 mL) and treated with Fmoc-3,4-diF-Phe-OH (220 mg, 0.52 mmol), HOBT (85 mg, 0.63 mmol), DIEA (162 mg, 1.25 mmol) and HBTU (237 mg, 0.63 mmol). The suspension was stirred at about rt for about 20 h, then filtered and washed with DMF, MeOH and DCM. The resulting resin was treated with 20% piperidine in DMF (4 mL) at about rt for about 2 h and then filtered, washed with DMF, MeOH, DCM and Et₂O to afford the resin AB4. To 4-Nitrophenyl chloroformate (157 mg, 0.78 mmol) in dry DCM (15 mL) at about –20° C., a solution of AA2 (Scheme AA, 291 mg, 1.0 mmol) and DIEA (291 mg, 2.25 mmol) in DCM (5 mL) was added dropwise. The mixture was stirred at about –20° C. for about 20 min and then the dipeptidyl resin AB4 was added. After additional stirring at about –20° C. for about 20 min, the reaction temperature was allowed to warm up to about rt slowly, then stirred at about rt for about 18 h. The suspension was filtered and washed with DMF, MeOH, DCM and Et₂O, then dried in vacuo to give the resin AB5. Half of the resin AB5 was treated with a solution of pyrrolidine (85 mg, 1.2 mmol) and formaldehyde (37%, 78 mg, 0.96 mmol) in 1,4-dioxane:glacial acetic acid (4:1; 4 mL). The suspension was stirred at about rt for about 18 h, then filtered, washed with MeOH, DCM and Et₂O and dried in vacuo. The resulting resin was treated with TFA:DCM:anisole (50:50:0.50, 5 mL) at about rt for about 1.5 h; then the reaction mixture was filtered and washed with fresh 30% TFA in DCM. The filtrates were combined and evaporated in vacuo, and the residue was triturated with diethyl ether (2×) to give the product Compound 6 as a light yellow solid. $^1$H NMR (CD₃OD) δ 7.81–6.95 (m, 13 H), 5.56 (s, 2 H), 5.05–4.80 (m, 3 H), 4.45 (s, 2 H), 3.45–2.82 (m, 10 H), 2.20–1.80 (m, 6 H). ES-MS m/z 753 (MH⁺).

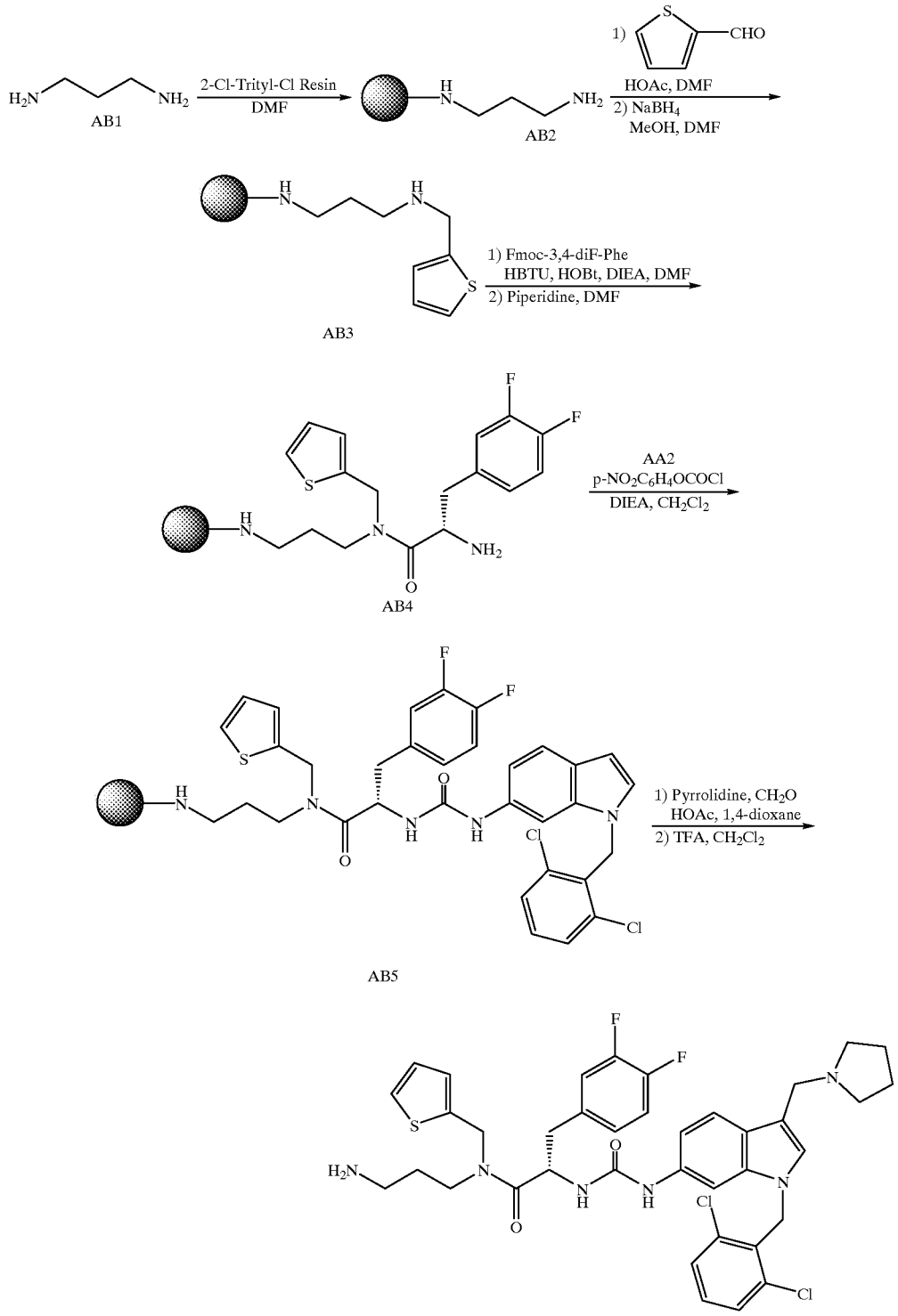

Example 3

As a specific embodiment of an oral composition, about 100 mg of the Compound 15 of Example 1 is formulated with sufficient finely divided lactose to provide a total amount of about 580 mg to about 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of the following formula (I):

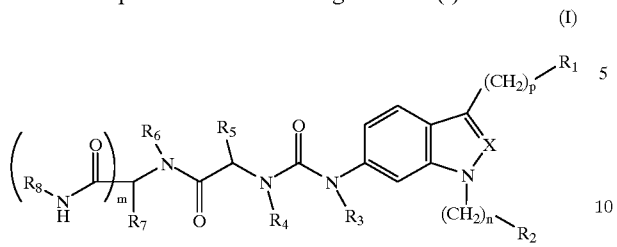

(I)

wherein:
R₁ is selected from the group consisting of amino, $C_1-C_8$ alkylamino, $C_1-C_8$ dialkylamino, arylamino, ar$C_1-C_8$ alkylamino, $C_3-C_8$ cycloalkylamino, heteroalkyl$C_1-C_8$ alkylamino, heteroalkyl $C_1-C_8$ alkyl-N-methylamino, $C_1-C_8$ dialkylamino $C_1-C_8$ alkylamino, —N($C_1-C_8$alkyl)—$C_1-C_8$alkyl-N($C_1-C_8$alkyl)₂, —N($C_1-C_8$ alkyl)($C_1-C_8$ alkenyl), —N($C_1-C_8$alkyl) ($C_3-C_8$cycloalkyl), heteroalkyl and substituted heteroalkyl, wherein the substituent on the heteroalkyl is selected from oxo, amino, $C_1-C_8$ alkoxy, $C_1-C_8$ alkyl, $C_1-C_8$ alkylamino or $C_1-C_8$ dialkylamino;

R₂ is selected from the group consisting of unsubstituted or substituted aryl, ar$C_1-C_8$ alkyl, $C_3-C_8$cycloalkyl and heteroaryl, wherein the substituents on the aryl, aralkyl, cycloalkyl or heteroaryl group are independently selected from the group consisting of one or more of halogen, nitro, amino, cyano, hydroxyalkyl, $C_1-C_8$ alkyl, $C_1-C_8$ alkoxy, $C_1-C_8$alkoxycarbonyl, acetyl, fluorinated $C_1-C_4$ alkyl, fluorinated $C_1-C_4$ alkoxy and $C_1-C_4$ alkylsulfonyl;

R₃ is selected from the group consisting of H and $C_1-C_8$ alkyl;

R₄ and R₅ are each independently selected from the group consisting of H, $C_1-C_8$ alkyl, amino$C_1-C_8$ alkyl, amidino$C_1-C_8$ alkyl, guanidino$C_1-C_8$ alkyl, aryl, ar$C_1-C_8$ alkyl, substituted aryl, substituted ar$C_1-C_8$, alkyl, heteroaryl, heteroaryl$C_1-C_8$ alkyl, substituted heteroaryl, substituted heteroaryl$C_1-C_8$ alkyl, $C_3-C_6$ cycloalkyl and substituted $C_3-C_6$cycloalkyl, wherein the substituents on the aryl, aralkyl, cycloalkyl or heteroaryl group are independently selected from the group consisting of one or more of halogen, nitro, amino, amidino, guanidino, cyano, hydroxyalkyl, $C_1-C_8$alkyl, $C_1-C_8$alkoxy, $C_1-C_8$alkoxycarbonyl, acetyl, fluorinated $C_1-C_4$ alkyl, fluorinated $C_1-C_4$ alkoxy and $C_1-C_4$ alkylsulfonyl;

R₆ and R₇ are each independently selected from the group consisting of H, $C_1-C_8$ alkyl, amino$C_1-C_8$ alkyl, amino$C_3-C_8$ cycloalkyl, amidino$C_1-C_8$ alkyl, guanidino$C_1-C_8$ alkyl, aryl, substituted aryl, ar$C_1-C_8$ alkyl, substituted ar$C_1-C_8$ alkyl, heteroaryl$C_1-C_8$ alkyl and substituted heteroaryl$C_1-C_8$ alkyl, wherein the one or more substituents on the aryl, aralkyl, cycloalkyl or heteroaryl group are independently selected from the group consisting of halogen, nitro, amino, amidino, guanidino, cyano, hydroxyalkyl, $C_1-C_8$ alkyl, $C_1-C_8$ alkoxy, $C_1-C_8$ alkoxycarbonyl, acetyl, fluorinated $C_1-C_4$ alkyl, fluorinated $C_1-C_4$ alkoxy and $C_1-C_4$ alkylsulfonyl;

R₈ is selected from the group consisting of H, $C_1-C_8$ alkyl, amino $C_1-C_8$ alkyl, allyl, $C_3-C_8$ cycloalkyl, substituted $C_3-C_8$ cycloalkyl, aryl, substituted aryl, $C_1-C_8$ alkyl, substituted ar$C_1-C_8$ alkyl, heteroaryl, substituted heteroaryl, heteroaryl$C_1-C_8$ alkyl and substituted heteroaryl$C_1-C_8$ alkyl, wherein the one or more substituents on the aryl, aralkyl, cycloalkyl or heteroaryl group are independently selected from the group consisting of halogen, nitro, amino, amidino, guanidino, cyano, hydroxyalkyl, $C_1-C_8$ alkyl, $C_1-C_8$ alkoxy, $C_1-C_8$ alkoxycarbonyl, acetyl, fluorinated $C_1-C_4$ alkyl, fluorinated $C_1-C_4$ alkoxy and $C_1-C_4$ alkylsulfonyl;

X is CH or N;

n is an integer selected from the group consisting of 0, 1, 2 and 3;

m is an integer selected from the group consisting of 0 and 1; and p is an integer selected from the group consisting of 1 and 2;

provided that when m is 1, then one of R₅ or R₇ must be hydrogen;

provided further that when R₅ is hydrogen, then R₄ cannot be hydrogen; and, when R₇ is hydrogen, then R₆ cannot be hydrogen;

and pharmaceutically acceptable salts thereof.

2. The compound of claim 1 wherein

R₁ is selected from the group consisting of dimethylamino, diethylamino, di-(n-propyl)amino,

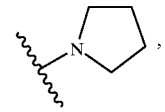

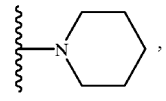

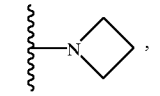

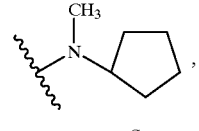

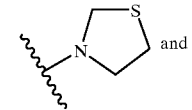 and

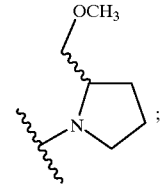

R₂ is selected from the group consisting of unsubstituted or substituted aryl, ar$C_1-C_6$ alkyl, $C_3-C_6$ cycloalkyl and heteroaryl, where the substituents on the aryl, aralkyl, cycloalkyl or heteroaryl group are independently selected from one to three substituents selected from the group consisting of halogen, cyano, $C_1-C_4$ alkyl, $C_1-C_4$ alkoxy, $C_1-C_4$ alkoxycarbonyl, fluorinated $C_1-C_4$ alkyl, fluorinated $C_1-C_4$ alkoxy and $C_1-C_4$ alkylsulfonyl;

R₃ is selected from the group consisting of H and $C_1-C_4$ alkyl;

R₄ and R₅ are each independently selected from the group consisting of H, $C_1-C_4$ alkyl, amino$C_1-C_6$ alkyl, amidino$C_1-C_6$ alkyl, guanidino$C_1-C_6$ alkyl, aryl, arC$_1$–C$_8$ alkyl, substituted aryl, and substituted arC$_1$–C$_8$ alkyl, wherein from one to two substituents on the aryl or aralkyl are independently selected from the group consisting of halogen, nitro, amino, amidino, guanidino, cyano, hydroxyalkyl, C$_1$–C$_6$ alkyl, C$_1$–C$_6$ alkoxy, C$_1$–C$_6$ alkoxycarbonyl, acetyl, fluorinated C$_1$–C$_4$ alkyl, fluorinated C$_1$–C$_4$ alkoxy and C$_1$–C$_4$ alkylsulfonyl;

R$_6$ and R$_7$ are each independently selected from the group consisting of H, C$_1$–C$_4$ alkyl, aminoC$_1$–C$_6$ alkyl, amidinoC$_1$–C$_6$ alkyl, guanidinoC$_1$–C$_6$ alkyl, aryl, substituted aryl, arC$_1$–C$_6$ alkyl, substituted arC$_1$–C$_6$ alkyl, C$_3$–C$_6$ cycloalkylC$_1$–C$_6$ alkyl, heteroarylC$_1$–C$_6$ alkyl and substituted heteroarylC$_1$–C$_6$ alkyl, wherein the one to two substituents on the aryl, aralkyl, or heteroaryl group are independently selected from the group consisting of halogen, nitro, amino, amidino, guanidino, cyano, hydroxyalkyl, C$_1$–C$_6$ alkyl, C$_1$–C$_6$ alkoxy, C$_1$–C$_6$ alkoxycarbonyl, acetyl, fluorinated C$_1$–C$_4$ alkyl, fluorinated C$_1$–C$_4$ alkoxy and C$_1$–C$_4$ alkylsulfonyl;

R$_8$ is selected from the group consisting of H, C$_1$–C$_6$ alkyl, aminoC$_1$–C$_6$ alkyl, aryl, substituted aryl, arC$_1$–C$_6$ alkyl, and substituted arC$_1$–C$_6$ alkyl, wherein one or more of the substituents on the aryl or aralkyl group are independently selected from the group consisting of halogen, nitro, amino, amidino, guanidino, cyano, hydroxyalkyl, C$_1$–C$_6$ alkyl, C$_1$–C$_6$ alkoxy, C$_1$–C$_6$ alkoxycarbonyl, acetyl, fluorinated C$_1$–C$_4$ alkyl, fluorinated C$_1$–C$_4$ alkoxy and C$_1$–C$_4$ alkylsulfonyl;

n and p are both 1;

provided that when m is one, then one of R$_5$ or R$_7$ must be hydrogen;

and provided further that when R$_5$ is hydrogen, then R$_4$ cannot be hydrogen; and, when R$_7$ is hydrogen, then R$_6$ cannot be hydrogen;

and pharmaceutically acceptable salts thereof.

3. The compound of claim 2, wherein

R$_1$ is 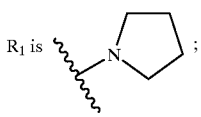 ;

R$_2$ is unsubstituted or substituted phenyl wherein the substituent is one or two substituents selected from the group consisting of fluorine, chlorine, iodine, methyl, cyano and trifluoromethyl;

R$_3$ is H;

R$_4$, R$_5$, R$_6$, and R$_7$ are each independently selected from the group consisting of H, aminoC$_1$–C$_5$ alkyl, amidinoC$_1$–C$_5$ alkyl, guanidinoC$_1$–C$_5$ alkyl, C$_3$–C$_6$ cycloalkylC$_1$–C$_6$ alkyl, heteroarylC$_1$–C$_6$ alkyl, benzyl and substituted benzyl wherein the substituents on the benzyl are one to two substituents independently selected from the group consisting of chlorine, fluorine, methyl and trifluoromethyl;

R$_8$ is benzyl;

provided that when m is one, then one of R$_5$ or R$_7$ must be hydrogen;

and provided further that when R$_5$ is hydrogen, then R$_4$ cannot be hydrogen; and, when R$_7$ is hydrogen, then R$_6$ cannot be hydrogen;

and pharmaceutically acceptable salts thereof.

4. The compound of claim 3, wherein

R$_2$ is 2,6-dichlorophenyl or 2-methylphenyl;

provided that when m is one, then one of R$_5$ or R$_7$ must be hydrogen;

and provided further that when R$_5$ is hydrogen, then R$_4$ cannot be hydrogen; and, when R$_7$ is hydrogen, then R$_6$ cannot be hydrogen;

and pharmaceutically acceptable salts thereof.

5. A pharmaceutical composition comprising a pharmaceutically acceptable carrier and a compound of claim 1.

6. A pharmaceutical composition made by mixing a compound of claim 1 and a pharmaceutically acceptable carrier.

7. A process for making a pharmaceutical composition comprising mixing a compound of claim 1 and a pharmaceutically acceptable carrier.

8. A method of treating a condition selected from the group consisting of thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder, neurodegenerative disorders, Angiogenesis related disorders and cancer in a subject in need thereof comprising administering to the subject a therapeutically effective amount of the compound of claim 1.

9. The method of claim 8, wherein the therapeutically effective amount of the compound is from about 0.1 mg/kg/day to about 300 mg/kg/day.

10. A method of treating a condition selected from the group consisting of thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder, neurodegenerative disorders, Angiogenesis related disorders and cancer in a subject in need thereof comprising administering to the subject a therapeutically effective amount of the composition of claim 5.

11. The method of claim 10, wherein the therapeutically effective amount of the compound is from about 0.1 mg/kg/day to about 300 mglkg/day.

12. A method of inhibiting platelet aggregation in a subject in need thereof comprising administering to the subject a therapeutically effective amount of the compound of claim 1.

13. The method of claim 12, wherein the therapeutically effective amount of the compound is from about 0.1 mg/kg/day to about 300 mg/kg/day.

14. A method of inhibiting platelet aggregation in a subject in need thereof comprising administering to the subject a therapeutically effective amount of the composition of claim 5.

15. The method of claim 14, wherein the therapeutically effective amount of the compound is from about 0.1 mg/kg/day to about 300 mg/kg/day.

16. A method of treating a condition mediated by thrombin receptor (PAR-1) in a subject in need thereof comprising administering to the subject a therapeutically effective amount of the compound of claim 1.

17. The method of claim 16, wherein the therapeutically effective amount of the compound is from about 0.1 mg/kg/day to about 300 mg/kg/day.

18. A method of treating a condition mediated by thrombin receptor (PAR-1) in a subject in need thereof comprising administering to the subject a therapeutically effective amount of the composition of claim 5.

19. The method of claim 18, wherein the therapeutically effective amount of the compound is from about 0.1 mg/kg/day to about 300 mg/kg/day.

* * * * *